(12) United States Patent
Sholev

(10) Patent No.: US 10,383,648 B2
(45) Date of Patent: Aug. 20, 2019

(54) STEERABLE MEDICAL DEVICE

(71) Applicant: Human Extensions Ltd., Netanya (IL)

(72) Inventor: Mordehai Sholev, Moshav Amikam (IL)

(73) Assignee: Human Extensions Ltd., Netanya (IL)

(*) Notice: Subject to any disclaimer, the term of this patent is extended or adjusted under 35 U.S.C. 154(b) by 318 days.

(21) Appl. No.: 14/765,842

(22) PCT Filed: Feb. 17, 2014

(86) PCT No.: PCT/IL2014/050224
§ 371 (c)(1),
(2) Date: Aug. 5, 2015

(87) PCT Pub. No.: WO2014/125498
PCT Pub. Date: Aug. 21, 2014

(65) Prior Publication Data
US 2015/0366572 A1 Dec. 24, 2015

Related U.S. Application Data

(60) Provisional application No. 61/765,745, filed on Feb. 17, 2013.

(51) Int. Cl.
A61B 17/29 (2006.01)
A61B 17/00 (2006.01)
(Continued)

(52) U.S. Cl.
CPC ........ A61B 17/29 (2013.01); A61B 17/00234 (2013.01); A61B 17/32 (2013.01);
(Continued)

(58) Field of Classification Search
CPC ............... A61M 25/0147; A61B 17/29; A61B 17/00234; A61B 17/32; A61B 34/71;
(Continued)

(56) References Cited

U.S. PATENT DOCUMENTS 3,631,737 A 1/1972 Wells
2003/0036748 A1 2/2003 Cooper et al.
(Continued)

FOREIGN PATENT DOCUMENTS

JP 2005-502398 1/2005
JP 2008-511404 4/2008
(Continued)

OTHER PUBLICATIONS

Notification of Office Action dated Jun. 22, 2017 From the State Intellectual Property Office of the People's Republic of China Re. Application No. 201480008853.8 and Its Summary in English. (4 Pages).
(Continued)

Primary Examiner — Anh T Dang

(57) ABSTRACT

A medical device and a system including same are provided. The medical device includes an elongated device body, at least a portion of which is steerable within a body of a subject via at least one control wire; and a plurality of control wire guides disposed along the elongated device body and being deployable to deflect the at least one control wire away from a longitudinal axis of the elongated device body.

16 Claims, 11 Drawing Sheets

(51) Int. Cl.
  *A61B 17/32* (2006.01)
  *A61B 34/00* (2016.01)
  *A61B 1/005* (2006.01)
  *A61B 1/008* (2006.01)
  *A61M 25/01* (2006.01)
  *A61B 34/30* (2016.01)

(52) U.S. Cl.
  CPC .............. *A61B 34/71* (2016.02); *A61B 1/008* (2013.01); *A61B 1/0055* (2013.01); *A61B 2017/003* (2013.01); *A61B 2017/00314* (2013.01); *A61B 2017/00323* (2013.01); *A61B 2017/2906* (2013.01); *A61B 2017/2927* (2013.01); *A61B 2034/306* (2016.02); *A61M 25/0147* (2013.01)

(58) Field of Classification Search
  CPC .............. A61B 1/008; A61B 2017/003; A61B 2017/00323; A61B 2017/00314; A61B 2034/306
  See application file for complete search history.

(56) References Cited

U.S. PATENT DOCUMENTS

| | | | |
|---|---|---|---|
| 2006/0074407 | A1 | 4/2006 | Padget et al. |
| 2006/0142789 | A1* | 6/2006 | Lehman ............ A61B 17/00234 606/153 |
| 2008/0051802 | A1 | 2/2008 | Schostek et al. |
| 2008/0091170 | A1 | 4/2008 | Vargas et al. |
| 2011/0118543 | A1 | 5/2011 | Dosher et al. |
| 2011/0213384 | A1* | 9/2011 | Jeong ..................... A61B 34/30 606/130 |
| 2012/0197239 | A1 | 8/2012 | Smith et al. |

FOREIGN PATENT DOCUMENTS

| | | |
|---|---|---|
| JP | 2009-509669 | 3/2009 |
| WO | WO 03/001986 | 1/2003 |
| WO | WO 2006/026520 | 3/2006 |
| WO | WO 2007/038715 | 4/2007 |
| WO | WO 2007/127199 | 11/2007 |
| WO | WO 2011/060124 | 5/2011 |
| WO | WO 2014/125498 | 8/2014 |

OTHER PUBLICATIONS

Translation of Notification of Office Action dated Jun. 22, 2017 From the State Intellectual Property Office of the People's Republic of China Re. Application No. 201480008853.8. (1 Page).
Communication Pursuant to Article 94(3) EPC dated Aug. 22, 2017 From the European Patent Office Re. Application No. 14751646.2. (5 Pages).
Notice of Reason for Rejection dated Aug. 29, 2017 From the Japan Patent Office Re. Application No. 2015-557569 and Its Translation Into English. (2 Pages).
Supplementary European Search Report and the European Search Opinion dated Sep. 7, 2016 From the European Patent Office Re. Application No. 14751646.2.
International Preliminary Report on Patentability dated Aug. 27, 2015 From the International Bureau of WIPO Re. Application No. PCT/IL2014/050224.
International Search Report and the Written Opinion dated Sep. 8, 2014 From the International Searching Authority Re. Application No. PCT/IL2014/050224.
Invitation to Pay Additional Fees dated Jun. 24, 2014 From the International Searching Authority Re. Application No. PCT/IL2014/050224.
Notification of Office Action and Search Report dated Jan. 4, 2017 From the State Intellectual Property Office of the People's Republic of China Re. Application No. 201480008853.8 and Its Translation of Office Action Into English. (12 Pages).
Notification of Office Action and Search Report dated Nov. 29, 2017 From the State Intellectual Property Office of the People's Republic of China Re. Application No. 201480008853.8. (7 Pages).
Translation of Notification of Office Action dated Nov. 29, 2017 From the State Intellectual Property Office of the People's Republic of China Re. Application No. 201480008853.8. (5 Pages).
Notification of Office Action dated May 2, 2018 From the State Intellectual Property Office of the People's Republic of China Re. Application No. 201480008853.8 and Its Translation Into English. (9 Pages).
Examination Report dated Jul. 25, 2018 From the Instituto Mexicano de la Propiedad Industrial, IMPI, Direccion Divisional de Patentes Re. Application No. MX/a/2015/010593 and Its Translation Into English. (6 Pages).

* cited by examiner

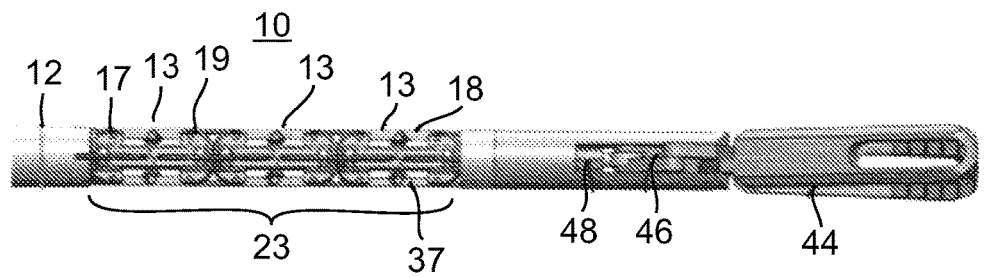
FIG. 4A
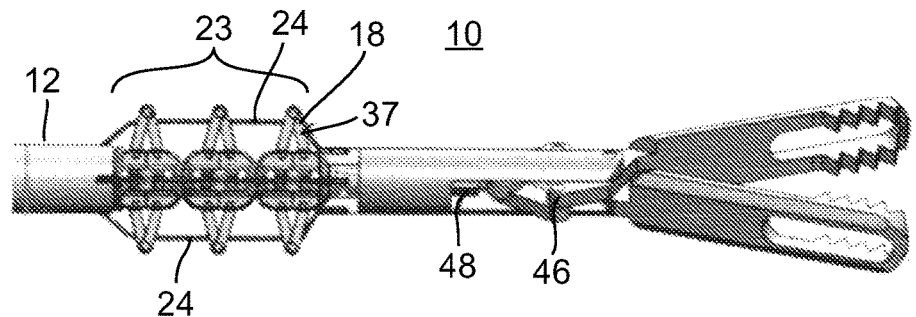
FIG. 4B
FIG. 4C
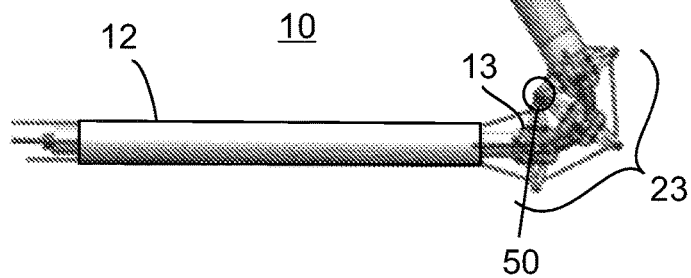

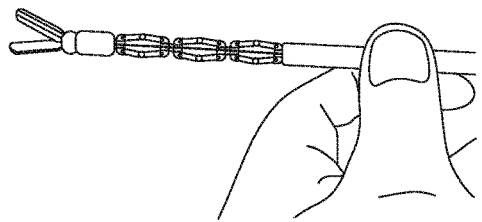
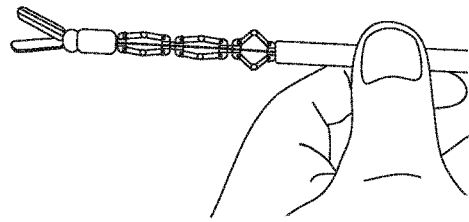
FIG. 7A　　　　　　　　FIG. 7B
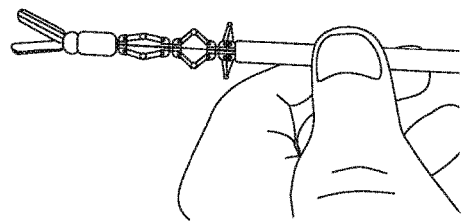
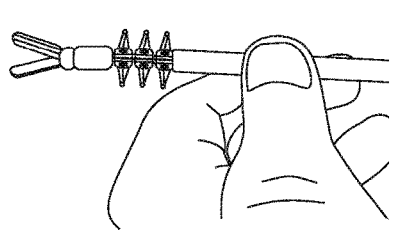
FIG. 7C　　　　　　　　FIG. 7D
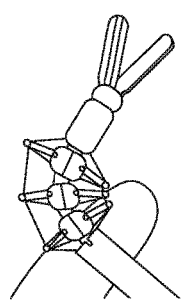
FIG. 7E

STEERABLE MEDICAL DEVICE

RELATED APPLICATIONS

This application is a National Phase of PCT Patent Application No. PCT/IL2014/050224 having International filing date of Feb. 17, 2014, which claims the benefit of priority under 35 USC § 119(e) of U.S. Provisional Patent Application No. 61/765,745 filed on Feb. 17, 2013. The contents of the above applications are all incorporated by reference as if fully set forth herein in their entirety.

FIELD AND BACKGROUND OF THE INVENTION

The present invention relates to a steerable medical device and, more particularly, to a medical device which includes radially deployable control wire guides.

Medical devices such as endoscopes and catheters are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered though a delivery port which is positioned through a small incision made in the tissue wall (e.g. abdominal wall), and are utilized in an anatomically constrained space, it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

In order to control deflection of a steerable portion of the device and thus steer the instrument mounted thereon, steerable medical devices typically employ one or more control wires which run the length of the device and terminate at the distal end of the steerable portion or at the distal tip.

The proximal end of each control wire is connected to the user operated handle; pulling of the wire bends the device body and deflects the steerable portion with relation the pulled wire.

Numerous examples of steerable devices are known in the art, see for example, U.S. Pat. Nos. 2,498,692; 4,753,223; 6,126,649; 5,873,842; 7,481,793; 6,817,974; 7,682,307 and U.S. Pat. Application Publication No. 20090259141.

Although prior art devices can be effectively steered inside the body, the relatively small diameter of the elongated device body (which is dictated by the diameter of the delivery port), severely limits angle-of-deflection capabilities and increases the pull force required to deflect the steerable device portion.

As such, it would be highly advantageous to have a steerable medical device having a device body narrow enough for delivery through standard delivery ports and yet capable of providing wide angle steering of the deflectable portion within the body while minimizing the pull force required for such steering.

SUMMARY OF THE INVENTION

According to one aspect of the present invention there is provided a medical device comprising: (a) an elongated device body, at least a portion of which being steerable within a body of a subject via at least one control wire; and (b) a plurality of control wire guides disposed along the elongated device body, the wire guides being deployable to deflect the at least one control wire away from a longitudinal axis of the elongated device body.

According to further features in preferred embodiments of the invention described below, at least a portion of the elongated device body is composed of a plurality of segments.

According to still further features in the described preferred embodiments the control wire guides form a part of the segments.

According to still further features in the described preferred embodiments the control wire guides extend radially outward when the plurality of interlinked segments are longitudinally compressed.

According to still further features in the described preferred embodiments the medical device further comprises a tube for compressing the interlinked segments.

According to still further features in the described preferred embodiments the control wire guides are attached to an external surface of the elongated device body.

According to still further features in the described preferred embodiments the control wire guides are struts capable of pivoting away from a longitudinal axis of the elongated device body.

According to still further features in the described preferred embodiments the pivoting of the struts is effected by pulling of the at least one control wire.

According to still further features in the described preferred embodiments the medical device further comprises a tubular sheath for compressing the struts against the elongated device body, wherein removal of the sheath releases the struts to pivot away from a longitudinal axis of the elongated device body.

According to still further features in the described preferred embodiments the medical device further comprises a plurality of control wires, each being for deflecting the at least a portion of the elongated device body in a specific direction.

According to still further features in the described preferred embodiments each of the plurality of control wires is deflectable via a specific set of control wire guides of the plurality of control wire guides.

According to still further features in the described preferred embodiments a number, spacing and/or deflection distance of control wire guides of the specific set of control wire guides varies for each of the plurality of control wires.

According to still further features in the described preferred embodiments the plurality of segments are interlinked.

According to still further features in the described preferred embodiments the elongated device body includes a flexible tube positioned through each of the plurality of segments.

According to still further features in the described preferred embodiments the medical device further comprises a tissue manipulator attached to a distal end of the elongated device body.

According to still further features in the described preferred embodiments the tissue manipulator is a grasper, a tissue cutter, or a needle.

According to another aspect of the present invention there is provided medical system comprising: (a) a first medical device having an elongated device body, at least a portion of the elongated device body being characterized by a first cross sectional shape; (b) a second medical device having an elongated device body, at least a portion of the elongated device body being characterized by a second cross sectional shape; wherein the first cross sectional shape and the second cross sectional shape are selected so as to maximize packing of at least one of the first medical device and at least one second medical device within an over tube.

According to still further features in the described preferred embodiments a portion of the elongated device body of the first medical device and/or the second medical device is steerable within a body of a subject.

According to still further features in the described preferred embodiments the over tube is used for delivering the first medical device and the second medical device into a body cavity.

According to still further features in the described preferred embodiments each of the first medical device and the second medical device further comprises a tissue manipulator attached to a distal end of the elongated device body.

According to still further features in the described preferred embodiments the tissue manipulator of the first medical device is different than a tissue manipulator of the medical device.

According to another aspect of the present invention there is provided a method of treating a subject: (a) delivering the medical device of claim 15 or the medical system of claim 20 into a body of the subject; and (b) using the tissue manipulator to surgically manipulate a target tissue thereby treating the subject.

The present invention successfully addresses the shortcomings of the presently known configurations by providing a steerable medical device having a deflectable region being configured capable of angling more than 180 degrees with respect to a longitudinal axis of the device.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4A-C illustrate a tissue grasper device composed of the segments shown in FIGS. 3A-B, shown in a delivery state (FIG. 4A), a deployed state (FIG. 4B), and a deflected state (FIG. 4C).

FIG. 6A is a cross section showing arrangement of the devices in the delivery tube; FIGS. 6B-C illustrate 2 configurations of steerable devices; and FIG. 6D illustrates coordinated use of several devices co-delivered through a delivery tube.

FIGS. 7A-E illustrate deployment (FIGS. 7A-D) and steering (FIG. 7E) of a prototype device constructed in accordance with the teachings of the present invention.

DESCRIPTION OF THE PREFERRED EMBODIMENTS

Figure 1A:
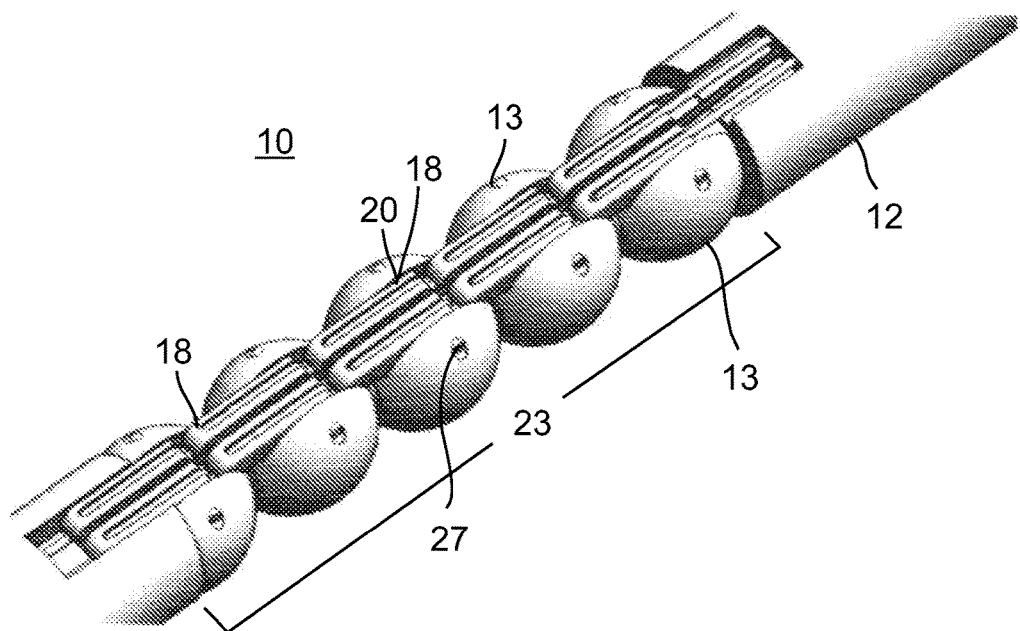
FIGS. 1A-B illustrate one embodiment of the device of the present invention in delivery (FIG. 1A) and deployed (FIG. 1B) states.

The present invention is of a medical device and system which can be used in minimally invasive surgery. Specifically, the present invention can be used to provide enhanced steering.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Steerable medical devices for use in minimally invasive surgery are well known in the art. Such devices typically utilize one or more control wires operable from a proximal end of the device positioned outside the body to deflect and thus steer a distal portion of the device positioned within the body. In order to enable the control wire to efficiently deflect the distal portion of the device, the longitudinal axis of the control wire must be offset from the axis of deflection. In general, the greater the offset, the more deflection can be achieved with less pulling force applied to the control wire.

Since the diameter of minimally invasive devices is dictated by the delivery port used to gain access to the intrabody tissues (typically 5, 8 or 10 mm), the offset between the control wire and the deflection axis is in fact limited by the diameter of such port and the configuration of the device.

To overcome this limitation, the present inventor has devised a unique control wire guide configuration which enables greater separation between the longitudinal axis of the control wire and the deflection axis of the device thus enabling greater deflection while greatly reducing the pulling force required to achieve such deflection.

Thus, according to one aspect of the present invention there is provided a medical device which includes a steerable intrabody portion capable of being steered through a wide range of angles (up to 180 degrees and more) and patterns such as zigzag or varied diameter curves at one or more points along its length.

As used herein, the phrase "medical device" refers to any device utilizable in treatment of a subject, preferably a human subject. The medical device of the present invention is preferably used in minimally invasive surgery wherein a steerable distal portion thereof positioned within a body of a subject is controlled from a proximal end positioned outside the body (extra corporeally) via a control mechanism which preferably includes control wires. The medical device can be used for viewing or for manipulating tissues within any body cavity. Examples of medical devices which can benefit from the present invention include an endoscope (e.g. laparoscope or thorascope), a catheter, a needle holder, grasper, Scissors, hook, stapler, retractor and the like.

The medical device of the present invention includes an elongated device body having a distal portion at least a portion of which is steerable within a body of a subject (also referred to herein as steerable portion), preferably via at least one control wire. As is further described herein, the steerable portion of the device can be deflected in various directions and configurations, e.g. the entire steerable portion can be deflected (arced) towards one direction using a single control wire, or a first segment of the steerable portion can be deflected in one direction while another can be deflected in an opposite direction (zigzag) using two or more control wires.

The elongated device body includes a plurality of control wire guides disposed along its length for routing one or more control wires from a proximal end of the elongated device body (which includes user controls, e.g. motorized or manual handle) to an end of a steerable portion thereof. In the case of a device which includes two or more separately steerable portions (e.g. zigzag-shaped deflection), each control wire is routed to an end of a respective steerable portion.

In any case, at least some of the control wire guides are deployable to deflect a control wire carried thereby away from a longitudinal axis of the elongated device body. Deflection of the control wire away from the longitudinal axis of the device (radially outward) increases the offset between the control wire and the deflection axis of the elongated device body and thus provides a wider range of deflection angles while minimizing the pulling force needed to achieve deflection.

As is described in detail below, the elongated device body is configured such that deployment of the control wire guides can be effected by a user following insertion of the distal portion of the device into the body. This enables delivery of the medical device of the present invention through a standard delivery port (e.g. 5, 8 or 10 mm trocar port).

Several configurations can be used to enable deflection of the control wire away from the longitudinal axis of the elongated body. Such configurations preferably utilize control wire guides that move radially outward while also spacing the wire guides away from each other along the length of the elongated body. As is further described hereinbelow, such spacing increases the angulation capabilities of the elongated body.

Referring now to the drawings, FIGS. 1a-5b illustrates several configurations of the present medical device which is referred to herein as device 10.

Figure 1B:
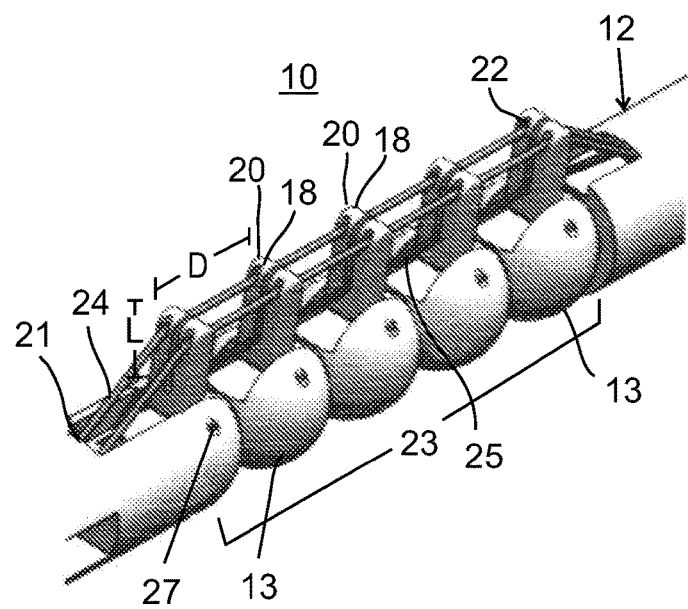

FIGS. 1a-b illustrate an embodiment of device 10 which employs control wire guides configured as fold-out struts.

Device 10 of FIGS. 1a-b includes an elongated device body 12 (also referred to herein as elongated body 12 or body 12) which can include a deflectable portion 23 fabricated from a flexible tube or rod, or a series of segments 13 (as shown in FIG. 1a-b).

Elongated device body 12 includes a user operable handle (see FIGS. 8a-b for an example) attached to proximal end thereof and an effector end (e.g. tissue manipulator such as a grasper) attached to a distal end (44 in FIGS. 4a-5b). The handle functions in controlling and setting an orientation and position of elongated body 12 and in operating the effector end.

A flexible tube/rod configuration of deflectable portion 23 can be fabricated from a polymer such as structural engineering polymer, polypropylene, polycarbonate and the like using molding or extrusion techniques. In order to increase the maximal deflection angle, deflectable portion 23 can also include cutouts along one or more sides of the tube (e.g. such as those shown in U.S. Pat. No. 4,911,148).

Elongated body 12 can be 20-40 cm in length and 2.5-12 mm in diameter. Elongated body 12 can be hollow or solid depending on the use of device 10. For example, in cases where device 10 is used to steer an endoscopic camera, elongated body 12 can be hollow in order to enable routing of wires or fiber optic cables from a user operable end (handle) to a camera or lens mounted on a distal end of elongated device body. A hollow elongated body 12 can also be used to route wires for controlling an operation of a tissue manipulator head such as a grasper although it will be appreciated that such wires can also be routed on the external surface of elongated body 12 through dedicated guides.

Elongated body 12 also includes two or more control wire guides 18 which in this embodiment of device 10 are configured as pivoting struts 20 (5 shown). Struts 20 can be fabricated from a polymer or alloy and can be attached to elongated body 12 using well known approaches. Alternatively, struts 20 can be co-formed with elongated device body 12 by, for example, cutting out struts 20 from the sidewall of a tube-shaped elongated body.

Struts 20 are folded against elongated body 12 (as shown in FIG. 1a) during delivery of device 10 through a delivery port and are capable of folding out and back to assume a deployed position (as shown in FIG. 1b) in which struts 20 are angled at about 90 degrees with respect to elongated device body 12. Struts can be connected to elongated body 12 via an elastic or pivoting hinge 27; a backstop can be provided on elongated body 12 to stop backward movement of strut 20 at about 90 degrees, or alternatively, the hinge can be designed for such purposes.

Struts 20 can be maintained folded against device body via a delivery over-tube or sheath or via a fastening mechanism. Alternatively, struts 20 can be spring loaded to assume a folded configuration. Struts 20 include holes 22 at a distal end thereof (2 shown for each strut 20) through which a control wire 24 (a pair of control wires 24 shown for each strut) can be threaded.

Control wires 24, which can be threaded through one or more rows of struts 20 (one row shown). One or more control wires 24 (two shown), threaded from the user handle through a single row of struts 20 (positioned on one side of elongated body 12 in the embodiment of FIGS. 1*a*-*b*) to an attachment point 21 at an end of the steerable portion, enables single-sided deflection (towards the side of struts 20) of a steerable portion of elongated body 12. Two or more control wires 24 threaded through two opposing rows enable bi-directional deflection. Any number of control wires can be used depending on the deflection direction and configuration desired. A device 10 having several deflectable portions each separately capable of bi-directional deflection is described hereinbelow with reference to FIGS. 5*a*-*b*.

Each strut 20 has a length L and a distance D from an adjacent strut 20 (FIG. 1*b*). Length L can be for example in the range of 1-5 mm, whereas distance D can be for example anywhere from 3 to 6 mm. Length L determines a leverage provided by strut 20 on a deflection point or region in elongated body 12 (for example, a point in a center of a width of elongated body 12 between segments 13), a larger L provides more leverage since the distance between the wire supported by strut 20 and the center of elongated body 12 is larger. Distance D determines the maximum angle of deflection of elongated body 12 (from the longitudinal axis) at the region of struts 20, a larger D enables a larger angle of deflection since contact between the tips of struts 20 will prevent further deflection.

The force needed to angle the links of a steerable segment of device 10 depends on the elastic properties of the steerable segment, and the distance between control wire 24 and a width center point of the steerable segment. This distance increases from length d to length D when struts 20 are deployed. The ratio d/D indicates the reduction in force needed to angle the links of a steerable segment.

For example: in simple joint of regular tool having shaft with 5 mm diameter with typical length of $$d=2.2_{mm}$$

If, for example, the force needed to angle the steerable segment is $F=10_N$, then the moment of angulation can be calculated by:

$$M \text{ bending}=F \times d_{regular\ shaft}$$

$$M \text{ bending}=10_N \times 0.022_M$$

$$M \text{ bending}=0.22_{NM}$$

If, for example, distance D is 6.6 mm, and the elastic properties of the steerable segment remain the same then the force needed to angle the steerable segment be calculated by:

$$M \text{ bending}=F \times D_{struts\ folded\ out}$$

$$0.22\ NM=F \times 0.066_M$$

$$F=0.22_{NM}/0.066_M$$

$$F=3.33_N$$

Device 10 can be deployed by pushing it out of the over-tube within the body cavity, or alternatively, in the case where struts 20 are fastened to, or spring-loaded against, elongated body 12, pulling of control wires 24 can release struts 20 and unfold them.

Device 10 can further include a wire for actuating a tissue manipulator end such an actuating wire can thread through center hole 15 (FIG. 2*a*) at each link 13.

Figure 2A:
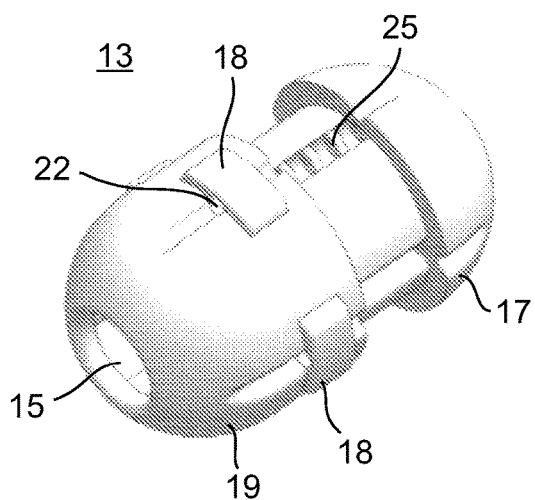
FIGS. 2A-B illustrate another embodiment of the device of the present invention showing a single segment with control wire guides in a delivery state (FIG. 2A) and a deployed device (FIG. 2B).
Figure 2B:
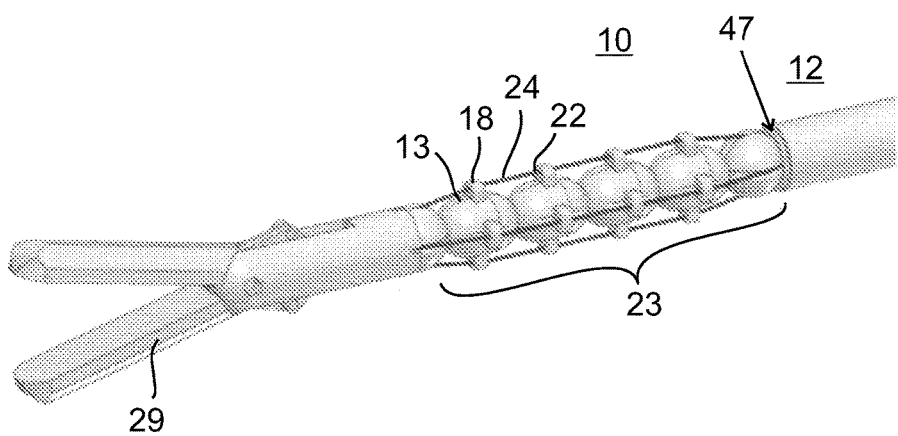

FIGS. 2*a*-*b* illustrate another embodiment of device 10. In this embodiment, device 10 includes an elongated body 12 (FIG. 2*b*) which is composed of segments 13 attached to a tissue grasper 29. Each segment 13 can be fabricated from an alloy (e.g. stainless steel) or a polymer with a diameter of 2.2 (folded) and 6.6 mm (deployed).

Segments 13 can be interlinked via linkage elements or fixable or movably mounted on a single long flexible rod or the actuating wire and/or elastic sleeve. Segment 13 shown in FIG. 2*a* includes a longitudinal opening 15 which can accommodate a flexible rod or tube or the actuating wire and/or elastic sleeve (not shown). Any number of segments 13 can be mounted in a series on the rod or tube. In the configuration shown in FIG. 2*b*, four segments 13 are mounted on a rod or tube to form a deflectable region 23 of device 10. Segments 13 include 4 deployable control wire guides 18 having holes 22 for control wires 24. Wire guides 18 are shown in a delivery (closed) state in FIG. 2*a* and in a deployed state in FIG. 2*b*.

Each segment 13 includes two interlocked portions, a proximal portion 17 and a distal portion 19. A spring 25 pushes portions 17 and 19 away from each other and maintains wire guides 18 closed against segment 13, alternatively, wire guides 18 can be wrapped with an elastic tube that would function as a spring to keep guides 18 in side link 13. Control wires 24 are threaded through holes 22 from the handle of device 10 (not shown) to distal region 21. When control wires 24 are pulled in the proximal direction, portions 17 and 19 of segments 13 are compressed against spring 25 and wire guides 18 are deployed radially outward thus deflecting outward the portion of control wires 24 spanning the deflectable region.

In order to push out wire guides 18 when compressed, proximal portion 17 of each segment 13 includes a four-sided wedge that resides within distal portion 19 and in contact with (and internal to) the internal end of wire guides 18. When portions 17 and 19 are compressed, the wedge slides further into distal portion 19 thus pushing wire guides 18 outward and out of segment 13.

Once deployed, guides 18 enable a user to pull each side of deflectable region 23 and thus steer it in any direction. Since the ends of segments 13 are rounded, and wire guides 18 of adjacent segments are distanced from each other, region 23 can be deflected more than 90 degrees in any direction. Such deflection can be used to position a tissue grasper 29 at anatomically constrained spaces, or loop a device around an organ, for example, loop a gastric band around a lower esophageal sphincter or fundus of a stomach.

Figure 3A:
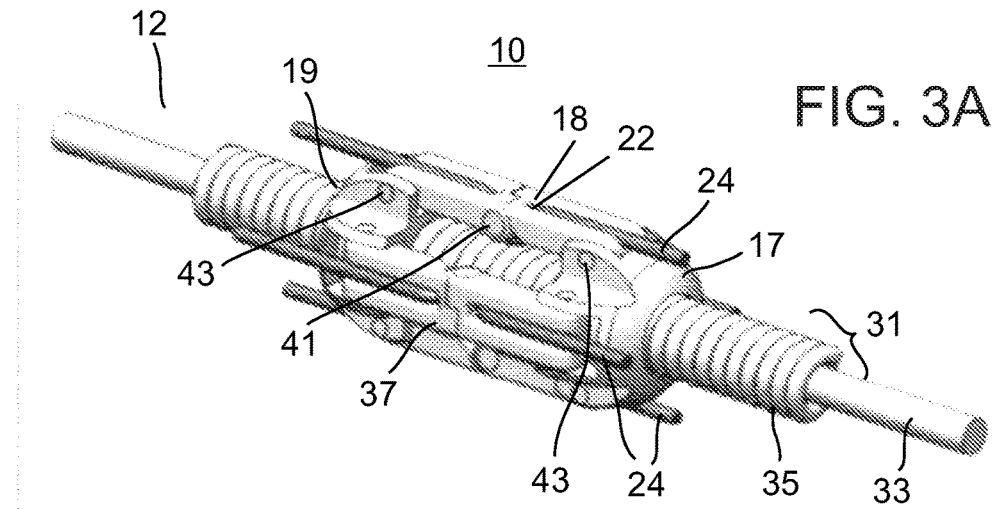
FIGS. 3A-C illustrate another embodiment of the device of the present invention showing a single segment with control wire guides in a delivery state (FIG. 3A), a single segment in a deployed state (FIG. 3B) and a segment configuration that includes a return spring (FIG. 3C).
Figure 3B:
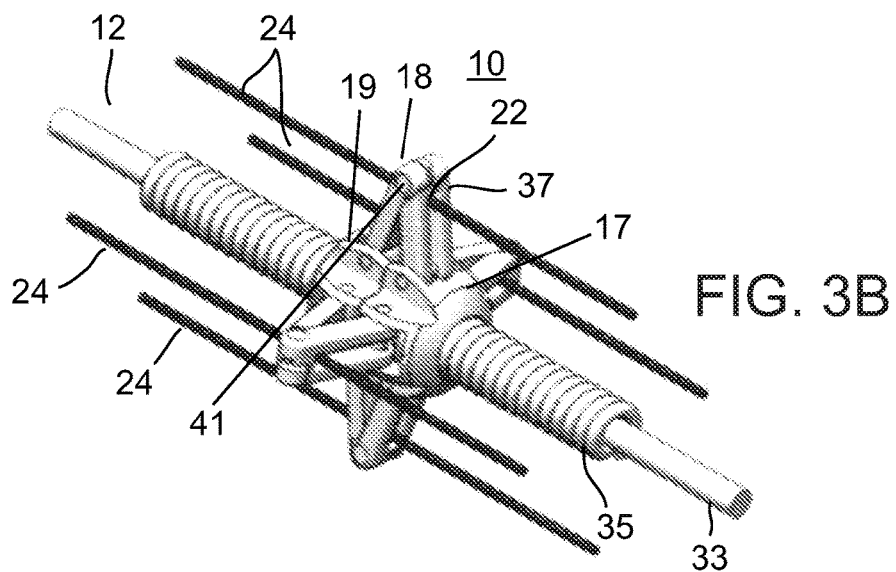
Figure 3C:
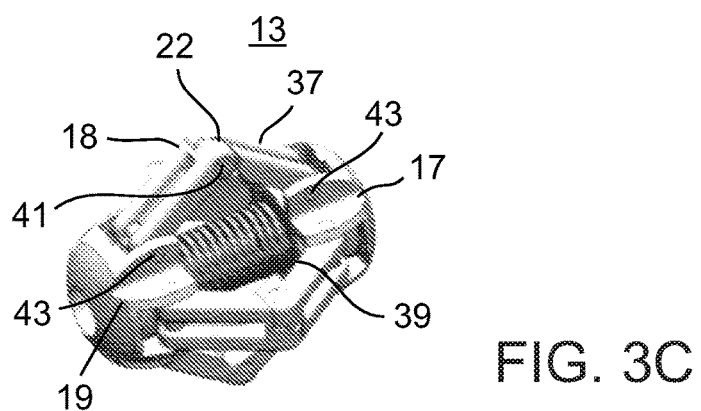

FIGS. 3*a*-*c* illustrate yet another configuration of device 10 which includes discrete segment 13 mounted over a flexible core 31 which includes a flexible tube/rod 33 surrounded by a spring like element 35.

Each segment 13 includes a proximal portion 17 and a distal portion 19 connected via one or more pivoting linkage arms 37 (Four shown in FIGS. 3*a*-*c*) which serve as control wire guides 18.

Control wires 24 run through holes 22 provided through linkage arms 37. When in a delivery state (FIG. 3*a*) linkage arms 37 are linearized and lie flat against spring-like element 35, while proximal and distal portions (17 and 19 respectively) are spaced apart. When distal portion 19 is pulled against proximal portion 17 linkage arms 37 pivot at midpoint pivot 41 and endpoint pivots 43 and extend radially outward thereby distracting control wires 24 away from the longitudinal axis of elongated body 12. Distal portion 19 can be pulled against proximal portion 17 by pulling on any one of control wires 24 or by pulling a separate deployment wire or by pushing proximal portion 17 towards distal portion 19 using internal tube 47 (shown in FIGS. 2*b*, and 4*a*-*b*).

In order to enable device 10 to assume a closed state for removal from the body cavity, segments 13 preferably include a spring 39 which is compressed when segments 13 are compressed (during deployment of linkage arms 37), releasing the deployment force (e.g. releasing a pull wire), spaces apart portions 17 and 19 thus returning linkage arms 37 to their linearized state.

FIGS. 4*a*-*c* illustrate a tissue manipulating device 10 which includes a deflectable region 23 composed of three segments 13 (similar to those shown in FIGS. 3*a*-*c* but with 2 wire guides 18 per segment 13). Device 10 can be configured as an endoscope, catheter or any other configuration deliverable into a body cavity, a vessel, a tissue and the like.

Device 10 includes a tissue manipulating head 44—tissue grasper head shown. Head 44 includes linkage mechanism 46, which is actuated via a dedicated wire 48, which runs within elongated body 12 to the user handle.

FIG. 4*a* illustrates device 10 in a delivery state with linkage arms 37 lying flat against elongate body 12 and portions 17 and 19 spaced apart. Following delivery into the body, pulling of control wires 24 or pushing internal tube 47 (FIG. 2*b*) compresses segments 13 and deploys wires 24 radially outward (FIG. 4*b*). Further pulling of one wire 24 (top wire 24 in FIG. 4*b*) deflects region 23 towards the pulled wire and may angles it more than 90 degrees with respect to a longitudinal axis of elongated body 12. Deflection is maximized to contact between guides 18 as indicated by 50 in FIG. 4*c*. The contact between guides 18 is used to keep the articulated joint in a rigid state both for pulling (against the tensioned control wires 24) or for pushing (against the body of levers 18).

Figure 5A:
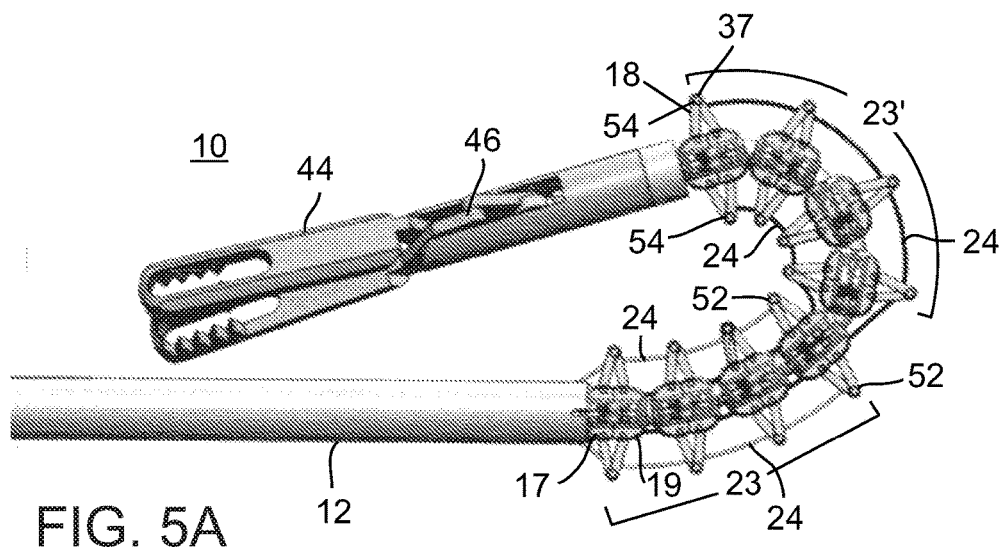
FIGS. 5A-B illustrate a device having 2 separately deflectable regions which can be deflected in the same direction (FIG. 5A) or in opposite directions (zigzag, FIG. 5B).
Figure 5B:
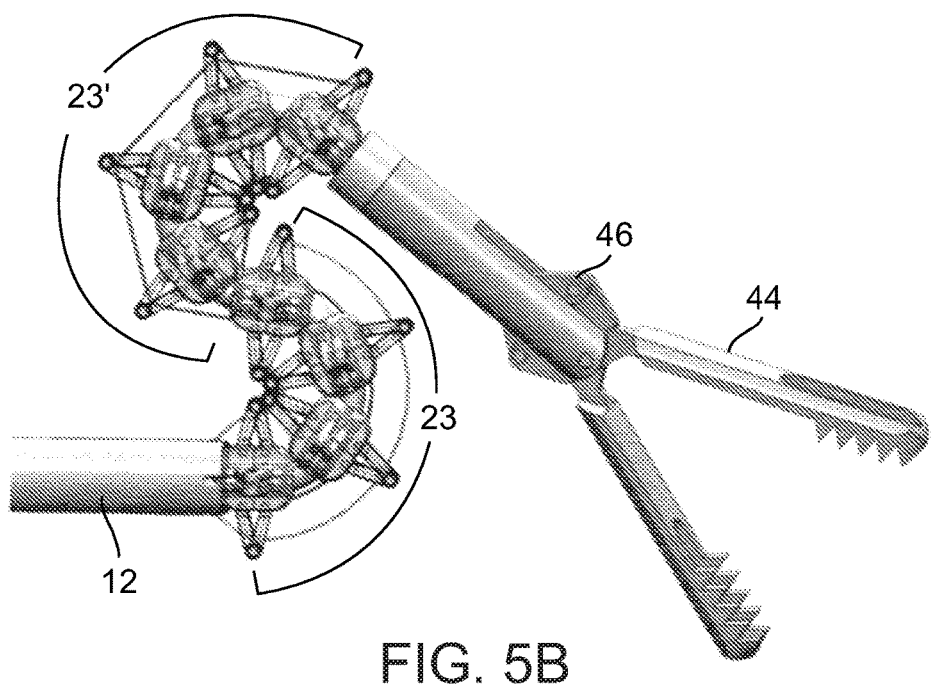

FIGS. 5*a*-*b* illustrate a device 10 that employs 8 segments 13 forming 2 separate deflectable regions 23 and 23'. Each of regions 23 and 23' are separately deflectable via a pair of dedicated control wires 24. A first pair of control wires 24 terminate at attachment points 52 (the distal most segment 13 of region 23), while a second pair of control wires 24 terminate at points 54 (the distal most segment 13 of region 23'). This enables a user to deflect both regions 23 and 23' in the same direction (FIG. 5*a*) enabling 180 degrees or more of deflection, or in opposite directions (zigzag, FIG. 5*b*). The latter enables insertion of the device 'behind' or around organs such as an intestine.

Thus, the present invention provides a steerable medical device that can be deployed through standard delivery port and yet provides superior steerability especially in tight anatomical spaces while requiring far less activation force to steer.

The medical device of the present invention is particularly advantages in procedures which require steering through tight anatomical spaces and/or steering around an organ.

As is mentioned hereinabove, control wires 24 of device 10 are preferably actuated from the user end of device 10 using a handle or a hand held motorized tool.

Figure 8A:
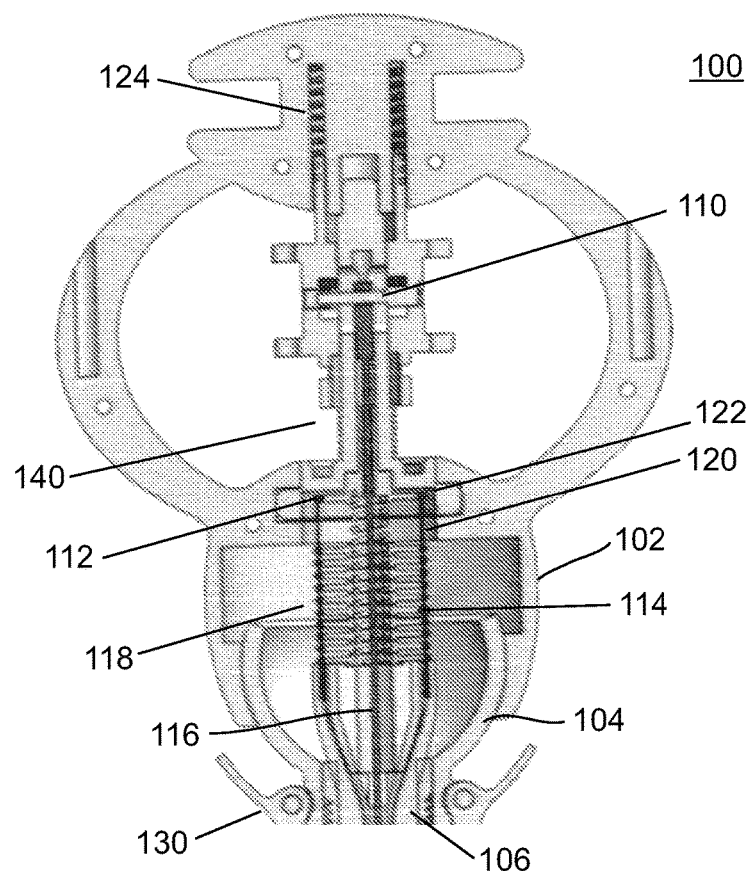
FIGS. 8A-B illustrate one embodiment of the present device showing the internal components of a handle (FIG. 8A), and the handle attached to the proximal end of the elongated body of the present device (FIG. 8B).
Figure 8B:
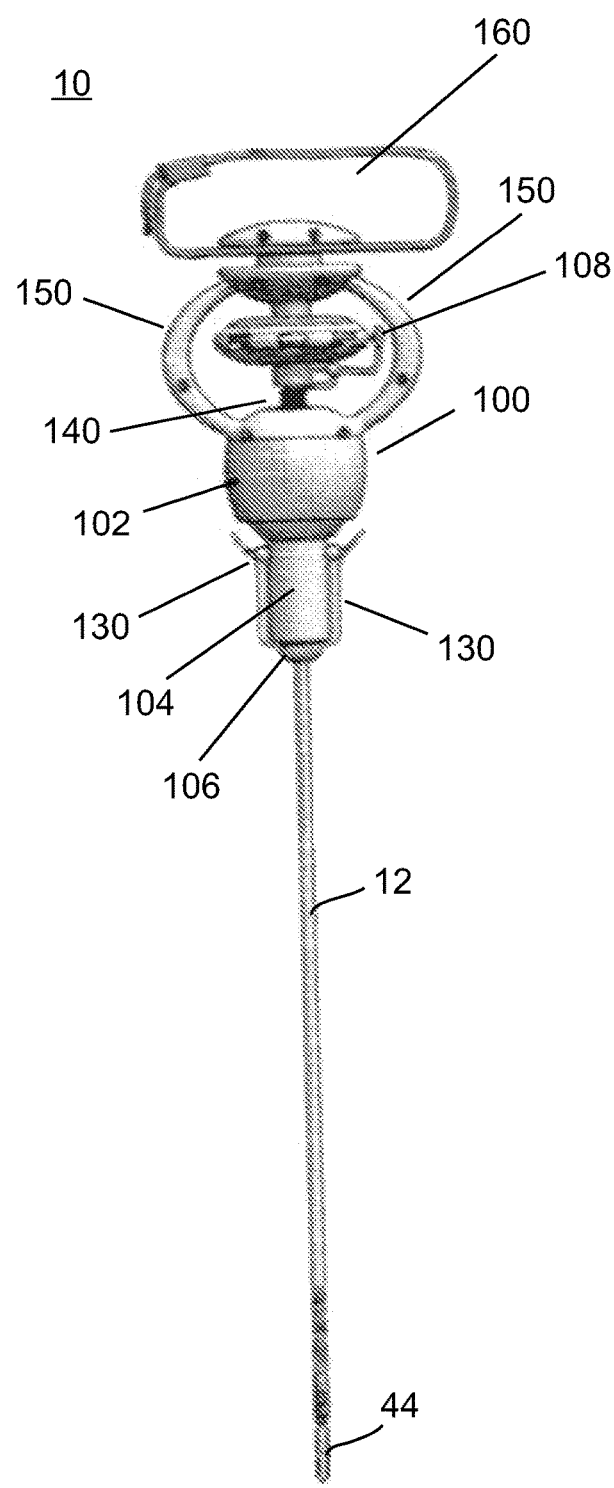

FIG. 8*a* illustrates one handle configuration that can be used with the present device. FIG. 8*b* illustrates the handle attached to the proximal end of elongated body 12 which includes a tissue manipulator 44 attached to its distal end.

FIG. 8*a*-*b* show handle 100 and related components. Handle 100 includes a handle housing 102 that contains shaft housing 104. Shaft housing 104 contains flexible core 118 compensating mechanism 112 wires 120 and wire ends 122. Wire ends 122 are locked into compensating mechanism 112, through holes located at the circumstance of flexible core 118. Wires 120 extend through struts 20 and are locked to an end strut or the distal end of elongated body 12 or tool tip housing. Handle housing 102 and shaft housing 104 forms a ball joint.

Following insertion of device 10 into the body cavity, shaft adapter 106 (hingedly locked to handle 102 through locking mechanism 130) is advanced in a distal direction to deploy struts 20 (to a deployed state set by the surgeon). Once struts 20 are deployed, compensating mechanism 112 moves in order to allow the deployment of the struts, while keeping the tension in wires 120. The surgeon can then articulate the distal joint by exerting a force on handle 102 causing the flexible core 118 to bend which causes the pulling of wires on the longer side of flexible core 118. The pulled wire pulls the distal end of elongated body 12 and angles elongated body 12. When the surgeon reduces the force on handle 102, central elastic element 114 and flexible core 118 return to their original state. The amount of deflection in flexible core 118 determines the pulling force on the control wire and the radius of angulation.

The proximal end of push/pull rod 116 is connected to jaws button 108 (mounted on jaws button shaft 140) through pin 110. When the surgeon moves jaws button 108 forward by sliding on jaws button shaft 140, the distal end (48, FIG. 4*b*) of push/pull rod 116, actuates jaw levers (46, FIG. 4*b*) which actuate jaws 44. A spring 124 can be used to facilitate the forward movement of jaws button 108. Rotating jaws button 108 rotates jaws 44 via pin 110 that transfers the rotation movement to the jaws via push/pull rod 116.

Device 10 of the present invention also provides advantages when using a motorized handle to steer elongated body 12 and actuate tissue manipulator 44. Since the force needed to navigate elongated body 12 is substantially less than that need in prior art devices a smaller lighter motor that can be easily integrated into the handle can be used.

Figure 6A:
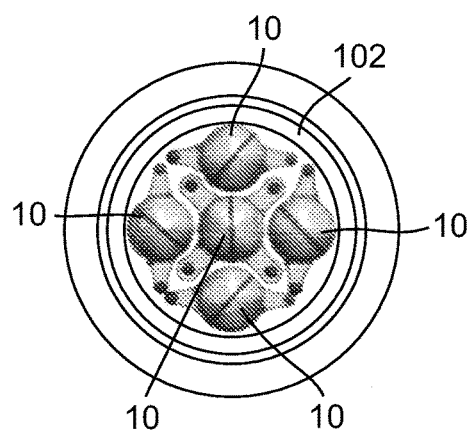
FIGS. 6A-D illustrate a system which includes several steerable devices configured for packing into a delivery tube.
Figure 6B:
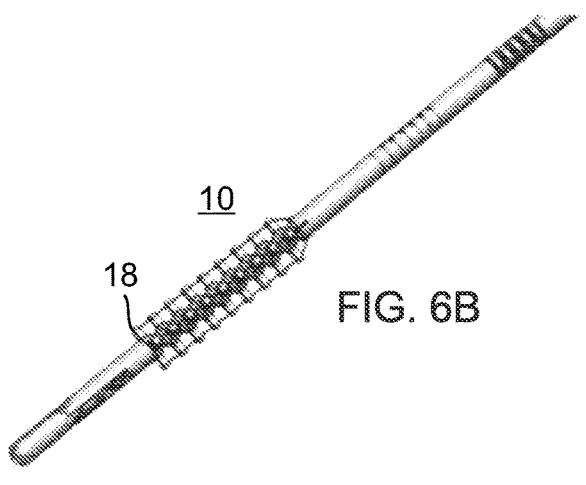
Figure 6C:
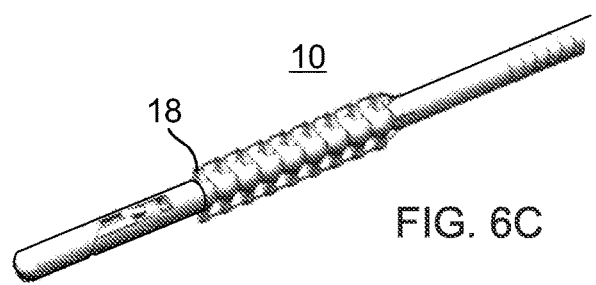

Steerable medical devices having external control wire guides that are deployable (as describe above) or preferably fixed in an outward configuration (as shown in FIGS. 6*b*-*c*), can be packed as a system in a delivery tube. Such a system, which is referred to herein as system 10 is shown in FIGS. 6*a* and *d*).

By utilizing a combination of two or more device configurations (two types shown in FIGS. 6*b*-*c*), two or more devices (five shown in the cross sectional view of FIG. 6*a* and the isometric view of FIG. 6*d*) can be efficiently packed in a single delivery tube 102. For example, system 100 shown in FIGS. 6*a* and 6*d* includes one device 10 having 4 rows of guides 18 and hence 4 control wires 24 (FIG. 6*b*), and four of device 10 which includes 2 rows of guides 18 and hence 2 control wires 24 (FIG. 6*c*).

Device 10 having 4 rows of guides 18 can be positioned in the middle of delivery tube 102, while the four device 10 having 2 rows of guides each, can be positioned there around. This maximizes packing of the devices in delivery tube 102 and enables delivery of several steerable devices having one or more steering capabilities into a body cavity through a standard delivery port.

Figure 6D:
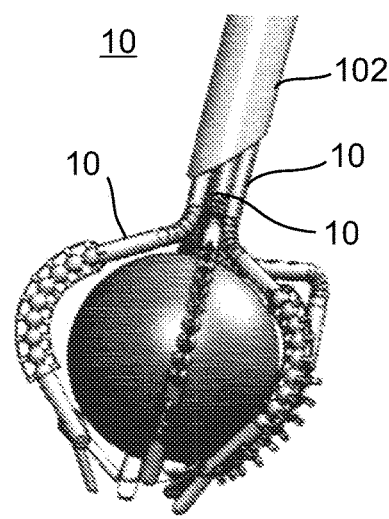

Devices 10 of system 100 can be used separately, i.e. each can be manipulated separately, or as is shown in FIG. 6*d*, devices 10 can be cooperatively manipulated (via a single system handle or five device-dedicated handles) to enable tissue manipulation not possible with a single device.

Device 10 can be operated using a manual or motorized handle. One example of a manually operated handle is illustrated in FIGS. 8*a*-*b* above.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

Prototype Grasper

Figure 9A:
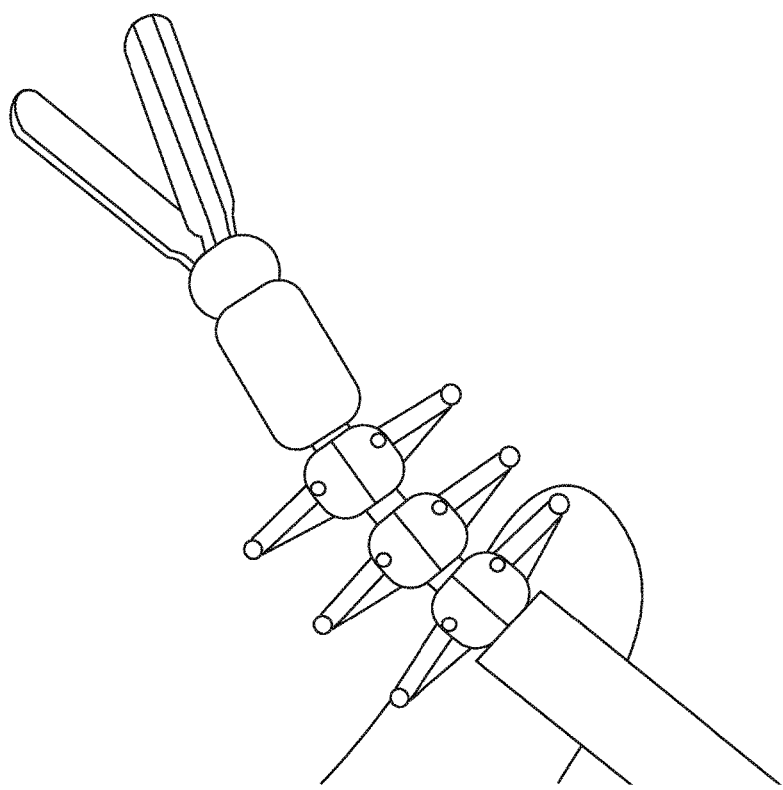
FIGS. 9A-B illustrate a prototype of one configuration of the present device.
Figure 9B:
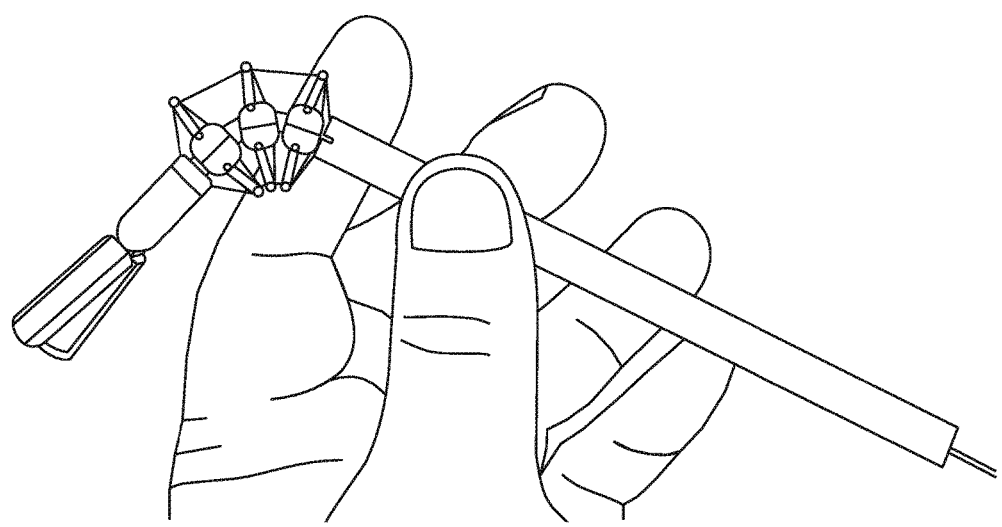

The configuration illustrated in FIGS. 7a-e was fabricated using rapid prototype technology (FIGS. 9a-b). Shaft and links body diameter was 7 mm when the struts are folded the tool can be inserted through port with inner canal having 7 mm diameter. When the struts are fully deployed, the distance between the wire and center of the steerable segment is 8 mm. The steerable segment was easily articulated (FIG. 9b) by pulling the control wires and the tissue grasper end was rotated and actuated using a central wire.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A medical device comprising:
   (a) an elongated device body, at least a portion of which being steerable within a body of a subject via at least one control wire; and
   (b) a plurality of control wire guides disposed along said elongated device body, said wire guides being deployable to move radially outward and away from an external surface of said elongated device body so as to move said at least one control wire away from said external surface of said elongated device body, wherein movement of said at least one control wire away from said elongated body decreases a pull force required for steering said steerable portion and offsets a longitudinal axis of said at least one control wire from an axis of deflection of said steerable portion.

2. The medical device of claim 1, wherein at least a portion of said elongated device body is composed of a plurality of segments.

3. The medical device of claim 2, wherein said control wire guides form a part of said segments.

4. The medical device of claim 3, wherein said control wire guides are attached to said elongated device body via a pivoting hinge and extend radially outward from said external surface of said elongated device body when said plurality of interlinked segments are longitudinally compressed.

5. The medical device of claim 4, further comprising a tube for compressing said interlinked segments.

6. The medical device of claim 2, wherein said plurality of segments are interlinked.

7. The medical device of claim 2, wherein said elongated device body includes a flexible tube positioned through each of said plurality of segments.

8. The medical device of claim 1, wherein said control wire guides are attached to an external surface of said elongated device body via a pivoting hinge.

9. The medical device of claim 1, wherein said control wire guides are struts capable of pivoting away from a longitudinal axis of said elongated device body.

10. The medical device of claim 9, wherein said pivoting of said struts is effected by pulling of said at least one control wire.

11. The medical device of claim 9, further comprising a tubular sheath for compressing said struts against said elongated device body, wherein removal of said sheath releases said struts to pivot away from a longitudinal axis of said elongated device body.

12. The medical device of claim 1, comprising a plurality of control wires, each being for deflecting said at least a portion of said elongated device body in a specific direction.

13. The medical device of claim 12, wherein each of said plurality of control wires is deflectable via a specific set of control wire guides of said plurality of control wire guides.

14. The medical device of claim 13, wherein a number, spacing and/or deflection distance of control wire guides of said specific set of control wire guides varies for each of said plurality of control wires.

15. The medical device of claim 1, further comprising a tissue manipulator attached to a distal end of said elongated device body.

16. The medical device of claim 15, wherein said tissue manipulator is a grasper, a tissue cutter, or a needle.

* * * * *